United States Patent
Kodokian et al.

(10) Patent No.: US 8,431,114 B2
(45) Date of Patent: Apr. 30, 2013

(54) POLYSACCHARIDE-BASED POLYMER TISSUE ADHESIVE FOR MEDICAL USE

(75) Inventors: George K. Kodokian, Kennett Square, PA (US); Samuel David Arthur, Wilmington, DE (US)

(73) Assignee: Actamax Surgical Materials, LLC, Berkeley, CA (US)

( * ) Notice: Subject to any disclaimer, the term of this patent is extended or adjusted under 35 U.S.C. 154(b) by 718 days.

(21) Appl. No.: 11/244,756

(22) Filed: Oct. 6, 2005

(65) Prior Publication Data

US 2006/0078536 A1  Apr. 13, 2006

Related U.S. Application Data

(60) Provisional application No. 60/616,899, filed on Oct. 7, 2004.

(51) Int. Cl.
*A61K 31/765* (2006.01)

(52) U.S. Cl.
USPC ...................................... 424/78.37

(58) Field of Classification Search .................. None
See application file for complete search history.

(56) References Cited

U.S. PATENT DOCUMENTS

| | | |
|---|---|---|
| 4,584,188 A | 4/1986 | Graham |
| 4,703,116 A | 10/1987 | Solarek et al. |
| 4,731,162 A | 3/1988 | Solarek et al. |
| 4,741,804 A | 5/1988 | Solarek et al. |
| 4,749,800 A | 6/1988 | Jobe et al. |
| 4,766,245 A | 8/1988 | Larkin et al. |
| 5,092,883 A | 3/1992 | Eppley et al. |
| 5,116,824 A | 5/1992 | Miyata et al. |
| 5,162,430 A | 11/1992 | Rhee et al. |
| 5,196,441 A | 3/1993 | Kunisch et al. |
| 5,275,838 A | 1/1994 | Merrill |
| 5,292,802 A | 3/1994 | Rhee et al. |
| 5,308,889 A | 5/1994 | Rhee et al. |
| 5,324,775 A | 6/1994 | Rhee et al. |
| 5,328,995 A | 7/1994 | Schaulin et al. |
| 5,451,398 A | 9/1995 | Vigh |
| 5,502,042 A | 3/1996 | Gruskin et al. |
| 5,505,952 A | 4/1996 | Jiang et al. |
| 5,514,379 A | 5/1996 | Weissleder et al. |
| 5,567,685 A | 10/1996 | Linden et al. |
| 5,643,575 A | 7/1997 | Martinez et al. |
| 5,733,563 A | 3/1998 | Fortier |
| 5,830,986 A | 11/1998 | Merrill et al. |
| 5,840,698 A | 11/1998 | Campbell et al. |
| 5,843,865 A | 12/1998 | Del Corral et al. |
| 5,874,500 A | 2/1999 | Rhee et al. |
| 6,051,648 A | 4/2000 | Rhee et al. |
| 6,121,375 A | 9/2000 | Eknoian |
| 6,150,472 A | 11/2000 | Engbers |
| 6,165,488 A | 12/2000 | Tardy et al. |
| 6,166,130 A | 12/2000 | Rhee et al. |
| 6,323,278 B2 | 11/2001 | Rhee et al. |
| 6,391,939 B2 | 5/2002 | Tayot et al. |
| 6,410,519 B1 | 6/2002 | Gruskin et al. |
| 6,458,147 B1 | 10/2002 | Cruise et al. |
| 6,458,889 B1 | 10/2002 | Trollsas et al. |
| 6,465,694 B1 | 10/2002 | Baudys et al. |
| 6,514,534 B1 | 2/2003 | Sawhney |
| 6,534,591 B2 | 3/2003 | Rhee et al. |
| 6,602,952 B1 | 8/2003 | Bentley et al. |
| 6,620,125 B1 | 9/2003 | Redl |
| 6,696,089 B2 | 2/2004 | Kabanov et al. |
| 6,703,047 B2 | 3/2004 | Sawhney et al. |
| 6,756,518 B2 | 6/2004 | Gruskin et al. |
| 6,800,278 B1 | 10/2004 | Perrault et al. |
| 6,833,408 B2 | 12/2004 | Sehl et al. |
| 6,858,736 B2 | 2/2005 | Nho et al. |
| 7,217,845 B2 | 5/2007 | Rosen et al. |
| 7,834,065 B2 | 11/2010 | Nakajima et al. |
| 2002/0151520 A1 | 10/2002 | Gruskin |
| 2003/0022216 A1 | 1/2003 | Mao et al. |
| 2003/0027788 A1 | 2/2003 | Singh et al. |
| 2003/0064502 A1 | 4/2003 | Illman et al. |
| 2003/0087111 A1 | 5/2003 | Hubbell et al. |
| 2003/0108511 A1 | 6/2003 | Sawhney |
| 2003/0119985 A1 | 6/2003 | Sehl et al. |
| 2004/0086479 A1 | 5/2004 | Grinstaff et al. |
| 2004/0096507 A1 * | 5/2004 | Kwang et al. ................. 424/486 |

(Continued)

FOREIGN PATENT DOCUMENTS

| | | |
|---|---|---|
| EP | 0961783 | 1/2007 |
| JP | 1982-102932 | 6/1982 |

(Continued)

OTHER PUBLICATIONS

Xiumei Mo et al., "Soft tissue adhesive composed of modified gelatin and polysaccharides", J. Biomater. Sci. Polymer Edn., vol. 11, No. 4, pp. 341-351 (2000).

(Continued)

*Primary Examiner* — Paul Dickinson
(74) *Attorney, Agent, or Firm* — McCarter and English

(57) ABSTRACT

Tissue adhesives formed by reacting an oxidized polysaccharide with a water-dispersible multi-arm polyether amine, wherein at least three of the arms are terminated by primary amine groups, are disclosed. The use of the tissue adhesives for medical and veterinary applications such as topical wound closure; and surgical procedures, such as intestinal anastomosis, vascular anastomosis, tissue repair, and ophthalmic procedures; drug delivery; anti-adhesive applications; and as a bulking agent to treat urinary incontinence are described.

47 Claims, No Drawings

U.S. PATENT DOCUMENTS

| | | | |
|---|---|---|---|
| 2004/0225097 A1* | 11/2004 | Nho et al. | 526/333 |
| 2004/0235708 A1 | 11/2004 | Rhee et al. | |
| 2005/0002893 A1* | 1/2005 | Goldmann | 424/70.27 |
| 2005/0020805 A1 | 1/2005 | Sunkara et al. | |
| 2005/0288684 A1 | 12/2005 | Aronson et al. | |
| 2006/0078536 A1 | 4/2006 | Kodokian et al. | |
| 2006/0115531 A1 | 6/2006 | Chenault | |
| 2006/0292030 A1 | 12/2006 | Odermatt et al. | |
| 2007/0031467 A1 | 2/2007 | Abrahams et al. | |
| 2007/0048251 A1 | 3/2007 | Arthur | |
| 2007/0249870 A1 | 10/2007 | Chenault | |
| 2008/0220047 A1 | 9/2008 | Sawhney et al. | |
| 2008/0319101 A1 | 12/2008 | Nakajima et al. | |
| 2009/0054535 A1 | 2/2009 | Figuly et al. | |
| 2010/0112063 A1 | 5/2010 | Figuly et al. | |
| 2011/0269916 A1 | 11/2011 | Chenault et al. | |

FOREIGN PATENT DOCUMENTS

| | | |
|---|---|---|
| JP | 1988-11167 | 1/1988 |
| WO | WO 87/00836 | 2/1987 |
| WO | WO 90/10441 | 9/1990 |
| WO | WO 91/15368 | 10/1991 |
| WO | WO 97/30103 | 8/1997 |
| WO | WO 99/01143 | 1/1999 |
| WO | WO 00/69925 | 11/2000 |
| WO | WO 01/49268 | 7/2001 |
| WO | WO 01/72280 | 10/2001 |
| WO | WO 01/87986 | 11/2001 |
| WO | WO02/102864 | 12/2002 |
| WO | WO 03/020818 | 3/2003 |
| WO | WO 03/035122 | 5/2003 |
| WO | WO 03/097759 | 11/2003 |
| WO | WO 2006/031358 | 3/2006 |
| WO | WO 2006/042161 | 4/2006 |
| WO | WO 2006/080523 | 8/2006 |
| WO | WO 2006/086510 | 8/2006 |
| WO | WO 2008/005207 | 1/2008 |
| WO | WO 2008/066787 | 6/2008 |
| WO | WO 2009/064977 | 5/2009 |
| WO | WO 2010/059279 | 5/2010 |
| WO | WO 2010/059280 | 5/2010 |
| WO | WO 2010/111570 | 9/2010 |
| WO | WO 2010/118284 | 10/2010 |

OTHER PUBLICATIONS

B. T. Hofreiter et al., "Rapid estimation of dialdehyde content of periodate oxystarch through quantitative alkali consumption", Anal. Chem., vol. 27, pp. 1930-1931 (1955).
Andreas F. Buckmann et al., "Functionalization of polyethylene glycol) and monomethoxy-poly(ethylene glycol)", Makromol. Chem., vol. 182, pp. 1379-1384 (1981).
Melvin A. Sarayba et al., "Inflow of ocular surface fluid through clear corneal cataract incisions: a laboratory model", Amer. J. Opthamol., vol. 138, pp. 206-210 (2004.
Jae Chan Kim et al., "Evaluation of tissue adhesives in closure of scleral tunnel incisions", J. Cataract Refract Surg., vol. 21, pp. 320-328 (1995).
Thomas Sweeney et al., "Intestinal anastomoses detected with a photopolymerized hydrogel", Surgery, vol. 131, No. 2, pp. 185-189 (2002).
J. Bruce et al., "Systematic review of the definition and measurement of anastomotic leak after gastrointestinal surgery", British Journal of Surgery, vol. 88, pp. 1157-1168 (2001).
Abstract, Kurisawa et al., Journal of Biomaterials Science, Polymer Edition 8/9:691-708 (1997).
Immunochemistry of Proteins, vol. 1, 1977, pp. 59-60, Plenum Press, New York, USA.
Thome, J., et al., "Ultrathin Antibacterial Polyammonium Coatings on Polymer Surfaces"; Surface and Coatings Technology, 174-175, 2003, pp. 584-587.
Harris, J. Milton, "Laboratory Synthesis of Polyethylene Glycol Derivatives", JMS—Rev., Macromol. Chem. Phys., C25 (3), 1985, pp. 325-373.
Harris, J. Milton, et al., "Synthesis of New Poly(Ethylene Glycol) Derivatives", PolyEthylene Glycol Chemistry: Biotechnical and Biomedical Applications, edited by Milton J. Harris, Plenum Press: New York, 1992, pp. 371-381.
Chen, Nicole, et al., "Mechanisms of Aldehyde-Containing Paper Wet-Strength Resins", Industrial & Engineering Chemistry Research, vol. 41, No. 22, 2002, pp. 5366-5371.
Callant, Dominique, et al., "A New Approach to Dextran Derivatives with Pendent Aldehyde Groups", Reactive Polymers, vol. 8, 1988, pp. 129-136.
Hollander, Andreas, et al., "Polymer Surface Chemistry for Biologically Active Materials", Applied Surface Science, vol. 235, 2004, pp. 145-150.
Stone, H. Harlan, et al., "Antibiotic Prophylaxis in Gastric, Biliary and Colonic Surgery", Ann. Surg; Oct. 1976, pp. 443-450.
Fishman, Alexander, et al., "Synthesis and Investigation of Novel Branched PEG-Based Soluble Polymer Supports", The Journal of Organic Chemistry, vol. 68, 2003, pp. 9843-9846.
Newkome, George R., "Improved Synthesis of an Ethereal Tetraamine Core for Dendrimer Construction", The Journal of Organic Chemistry, vol. 67, 2002, pp. 3957-3960.
Halabi, A., et al., "Synthesis and Characterization of a Novel Dendritic Acrylic Monomer", The Journal of Organic Chemistry, vol. 65, 2000, pp. 9210-9213.
Harris, J. Milton, et al., "Synthesis and Characterization of Poly(ethylene Glycol) Derivatives", Journal of Polymer Science: Polymer Chemistry Edition, vol. 22, 1984, pp. 341-352.
Merrill, Edward W., "Poly(ethylene oxide) Star Molecules: Synthesis, Characterization, and Applications in Medicine and Biology", Journal of Biomaterials Science Polymer Edition, vol. 5, No. 1/2, 1993, pp. 1-11.
Zhao, Xuan, et al., "Novel Degradable Poly(ethylene glycol) Esters for Drug Delivery", Poly(ethylene glycol) Chemistry and Biological Applications, Oxford University Press, 1998, Chapter 28, pp. 458-472.
Azzam, Tony, et al., "Cationic Polysaccharides for Gene Delivery", Macromolecules, vol. 35, No. 27, 2002, pp. 9947-9953.
Nagasaki, Yukio, et al., "Formyl-Ended Heterobifunctional Poly(ethylene oxide): Synthesis of Poly(ethylene oxide) with a Formyl Group at One End and a Hydroxyl Group at the Other End", Bioconjugate Chemistry, vol. 6, No. 2, 1995, pp. 231-233.
Greenwald, Richard B., et al., "Drug Delivery Systems Employing 1,4- or 1,6-Elimination: Poly(ethylene glycol) Prodrugs of Amine-Containing Compounds", Journal of Medicinal Chemistry, vol. 42, No. 18, 1999, pp. 3657-3667.
Zalipsky, Samuel, et al., "Preparation and Applications of Polyethylene Glycol—Polystyrene Graft Resin Supports for Solid-Phase Peptide Synthesis", Reactive Polymers, vol. 22, 1994, pp. 243-258.
Lara, V.S., et al., "Dentin-Induced In Vivo Inflammatory Response and In Vitro Activation of Murine Macrophages", Journal of Dental Research, vol. 82, No. 6, 2003, pp. 460-465.
Sweeney, Thomas, et al., "Intestinal Anastomoses Detected with a Photopolymerized Hydrogel", Surgery, vol. 131, No. 2, Feb. 2002, pp. 185-189.
Zhao, Huiru, et al., "Determination of Degree of Substitution of Formyl Groups in Polyaldehyde Dextran by the Hydroxylamine Hydrochloride Method", Pharmaceutical Research, vol. 8, No. 3, 1991, pp. 400-402.
Pfannemuller, B., et al., "Chemical Modification of the Surface of the Starch Granules", Starch/Starke, vol. 95, No. 9, 1983, pp. 298-303.

* cited by examiner

POLYSACCHARIDE-BASED POLYMER TISSUE ADHESIVE FOR MEDICAL USE

CROSS-REFERENCE TO RELATED APPLICATION

This application claims priority under 35 U.S.C. §119 from U.S. Provisional Application Ser. No. 60/616,899, filed Oct. 7, 2004.

FIELD OF THE INVENTION

The invention relates to the field of medical adhesives. More specifically, the invention relates to a polymer tissue adhesive formed by reacting an oxidized polysaccharide with a water-dispersible, multi-arm polyether amine.

BACKGROUND OF THE INVENTION

Tissue adhesives have many potential medical applications, including topical wound closure, supplementing or replacing sutures or staples in internal surgical procedures, adhesion of synthetic onlays or inlays to the cornea, drug delivery devices, and as anti-adhesion barriers to prevent post-surgical adhesions. Conventional tissue adhesives are generally not suitable for a wide range of adhesive applications. For example, cyanoacrylate-based adhesives have been used for topical wound closure, but the release of toxic degradation products limits their use for internal applications. Fibrin-based adhesives are slow curing, have poor mechanical strength, and pose a risk of viral infection. Additionally, the Fibrin-based adhesives do not covalently bind to the underlying tissue.

Several types of hydrogel tissue adhesives have been developed, which have improved adhesive and cohesive properties and are nontoxic. These hydrogels are generally formed by reacting a component having nucleophilic groups with a component having electrophilic groups, which are capable of reacting with the nucleophilic groups of the first component, to form a crosslinked network via covalent bonding. However, these hydrogels typically swell or dissolve away too quickly, or lack sufficient adhesion or mechanical strength, thereby decreasing their effectiveness as surgical adhesives.

Examples of hydrogel tissue adhesives are described by Sehl et al. in U.S. Patent Application Publication No. 2003/0119985. The adhesives are formed by reacting a hydrophilic polymer, such as collagen, with a crosslinkable component having nucleophilic groups and a crosslinkable component having electrophilic groups. The crosslinkable components include various activated forms of polyethylene glycol. Goldmann et al. in WO 03/035122 describe a hydrogel tissue adhesive formed by reacting chitosan or a modified polyvinyl alcohol bearing amino groups with an oxidized polysaccharide, such as oxidized dextran. Neither of these disclosures describes a polymer adhesive formed by reacting an oxidized polysaccharide with a water-dispersible, multi-arm polyether amine.

Therefore, the problem to be solved is to provide a tissue adhesive material with improved characteristics for use in surgical procedures as well as other medical applications.

Applicants have addressed the stated problem by discovering a polymer tissue adhesive formed by reacting an oxidized polysaccharide with a water-dispersible, multi-arm polyether amine, wherein at least three of the arms are terminated by a primary amine group. The resulting adhesive has improved adhesion and cohesion properties, crosslinks readily at body temperature, maintains dimensional stability initially, does not degrade rapidly, is nontoxic to cells and non-inflammatory to tissue.

SUMMARY OF THE INVENTION

The invention provides a kit comprising:
a) a first aqueous solution comprising an oxidized polysaccharide containing aldehyde groups, having a molecular weight of about 1,000 to about 1,000,000 Daltons, said oxidized polysaccharide having an equivalent weight per aldehyde group of about 90 to about 1500 Daltons, said solution containing from about 5% to about 40% by weight of the oxidized polysaccharide; and
b) a second aqueous solution comprising a water-dispersible, multi-arm polyether amine wherein at least three of the arms are terminated by a primary amine group, wherein the multi-arm polyether amine has a molecular weight of about 450 to about 200,000 Daltons, said solution containing from about 5% to about 70% by weight of the multi-arm polyether amine.

In another embodiment, the invention provides a method for applying a coating to an anatomical site on tissue of a living organism comprising: applying to the site a) a first aqueous solution comprising an oxidized polysaccharide containing aldehyde groups, having a molecular weight of about 1,000 to about 1,000,000 Daltons, said oxidized polysaccharide having an equivalent weight per aldehyde group of about 90 to about 1500 Daltons, said solution containing from about 5% to about 40% by weight of the oxidized polysaccharide, followed by b) a second aqueous solution comprising a water-dispersible, multi-arm polyether amine wherein at least three of the arms are terminated by a primary amine group, wherein the multi-arm polyether amine has a molecular weight of about 450 to about 200,000 Daltons, said solution containing from about 5% to about 70% by weight of the multi-arm polyether amine, or the aqueous solution of (b) followed by the aqueous solution of (a), or premixing the aqueous solutions of (a) and (b) and applying the resulting mixture to the site before the resulting mixture completely cures.

In another embodiment, the invention provides a method for bonding at least two anatomical sites together comprising: applying to at least one site a) a first aqueous solution comprising an oxidized polysaccharide containing aldehyde groups, having a molecular weight of about 1,000 to about 1,000,000 Daltons, said oxidized polysaccharide having an equivalent weight per aldehyde group of about 90 to about 1500 Daltons, said solution containing from about 5% to about 40% by weight of the oxidized polysaccharide; applying to a least one of either the same site or one other site b) a second aqueous solution comprising a water-dispersible, multi-arm polyether amine wherein at least three of the arms are terminated by a primary amine group, wherein the multi-arm polyether amine has a molecular weight of about 450 to about 200,000 Daltons, said solution containing from about 5% to about 70% by weight of the multi-arm polyether amine; or premixing the solutions of (a) and (b) and applying the resulting mixture to at least one site before the resulting mixture completely cures; and contacting the at least two anatomical sites together.

In another embodiment, the invention provides a composition comprising the reaction product of: a) a first aqueous solution comprising an oxidized polysaccharide containing aldehyde groups, having a molecular weight of about 1,000 to about 1,000,000 Daltons, said oxidized polysaccharide having an equivalent weight per aldehyde group of about 90 to about 1500 Daltons, said solution containing from about 5% to about 40% by weight of the oxidized polysaccharide; and b) a second aqueous solution comprising a water-dispersible, multi-arm polyether amine wherein at least three of the arms are terminated by a primary amine group, wherein the multi-arm polyether amine has a molecular weight of about 450 to about 200,000 Daltons, said solution containing from about 5% to about 70% by weight of the multi-arm polyether amine.

Methods for using the polymer tissue adhesive of the invention for topical wound closure, intestinal and vascular anastomoses, sealing corneal incisions, preventing adhesions, drug delivery, and treating urinary incontinence are also provided.

DETAILED DESCRIPTION OF THE INVENTION

The invention relates to a polymer adhesive formed by reacting an oxidized polysaccharide with a water-dispersible, multi-arm polyether amine, wherein at least three of the arms are terminated by a primary amine group. The polymer adhesive of the invention is useful as an adhesive for medical and veterinary applications including, but not limited to, topical wound closure, and surgical procedures, such as intestinal anastomosis, vascular anastomosis, tissue repair, and ophthalmic procedures. Additionally, the polymer adhesive may have utility in drug delivery, anti-adhesive applications, and as a bulking agent to treat urinary incontinence.

The following definitions are used herein and should be referred to for interpretation of the claims and the specification.

The term "oxidized polysaccharide" refers to a polysaccharide which has been reacted with an oxidizing agent to introduce aldehyde groups into the molecule.

The term "equivalent weight per aldehyde group" refers to the molecular weight of the oxidized polysaccharide divided by the number of aldehyde groups introduced in the molecule.

The term "water-dispersible, multi-arm polyether amine" refers to a branched polyether, wherein at least three of the branches ("arms") are terminated by a primary amine group, which is water soluble or able to be dispersed in water to form a colloidal suspension capable of reacting with a second reactant in aqueous solution.

The term "dendritic polyether" refers to a highly branched polyether having a tree-like structure.

The term "comb polyether" refers to a polyether having a main chain with multiple trifunctional branch points from each of which a linear arm emanates.

The term "star polyether" refers to polyether having a single branch point from which linear arms emanate.

The term "molecular weight" as used herein refers to the weight average molecular weight.

The term "% by weight" as used herein refers to the weight percent relative to the total weight of the solution, unless otherwise specified.

The term "anatomical site" refers to any external or internal part of the body of humans or animals.

The term "tissue" refers to any tissue, both living and dead, in humans or animals.

The term "hydrogel" refers to a water-swellable polymeric matrix, consisting of a three-dimensional network of macromolecules held together by covalent or non-covalent crosslinks, that can absorb a substantial amount of water to form an elastic gel.

The invention provides a tissue adhesive formed by reacting an oxidized polysaccharide with a multi-arm polyether amine, wherein at least three of the arms are terminated by a primary amine group. The reaction forms a hydrogel, which has many desirable characteristics as a tissue adhesive, including but not limited to improved adhesion and cohesion properties, crosslinks readily at body temperature, maintains dimensional stability initially, does not degrade rapidly, is nontoxic to cells and non-inflammatory to tissue.

Oxidized Polysaccharides:

Polysaccharides useful in the invention include, but are not limited to, dextran, chitin, starch, agar, cellulose, and hyaluronic acid. These polysaccharides are available commercially from sources such as Sigma Chemical Co. (St Louis, Mo.). In one embodiment, the polysaccharide is dextran. Suitable polysaccharides have a molecular weight from about 1,000 to about 1,000,000 Daltons, and in addition from about 3,000 to about 250,000 Daltons.

The polysaccharide is oxidized to introduce aldehyde groups using any suitable oxidizing agent, including but not limited to, periodates, hypochlorites, ozone, peroxides, hydroperoxides, persulfates, and percarbonates. In one embodiment, the polysaccharide is oxidized by reaction with sodium periodate, for example as described by Mo et al. (*J. Biomater. Sci. Polymer Edn.* 11:341-351, 2000). The polysaccharide is reacted with different amounts of periodate to give polysaccharides with different degrees of oxidation and therefore, different amounts of aldehyde groups, as described in detail in the General Methods Section of the Examples infra. The aldehyde content of the oxidized polysaccharide may be determined using methods known in the art. For example, the dialdehyde content of the oxidized polysaccharide may be determined using the method described by Hofreiter et al. (*Anal Chem.* 27:1930-1931, 1955), as described in detail in the General Methods Section of the Examples infra. In that method, the amount of alkali consumed per mole of dialdehyde in the oxidized polysaccharide, under specific reaction conditions, is determined by a pH titration. In one embodiment, the equivalent weight per aldehyde group of the oxidized polysaccharide is from about 90 to about 1500 Daltons.

In the invention, the oxidized polysaccharide is used in the form of an aqueous solution. The oxidized polysaccharide is added to water to give a concentration of about 5% to about 40% by weight, in addition from about 15% to about 30% by weight relative to the total weight of the solution. The optimal concentration to be used depends on the application and on the concentration of the multi-arm polyether amine used, as described infra, and can be readily determined by one skilled in the art using routine experimentation.

For use on living tissue, it is preferred that the aqueous solution comprising the oxidized polysaccharide be sterilized to prevent infection. Any suitable sterilization method known in the art that does not degrade the polysaccharide may be used, including, but not limited to, electron beam irradiation, gamma irradiation, ethylene oxide sterilization, or ultra-filtration through a 0.2 μm pore membrane.

The aqueous solution comprising the oxidized polysaccharide may further comprise various additives depending on the intended application. Preferably, the additive is compatible with the oxidized polysaccharide. Specifically, the additive does not contain primary or secondary amine groups that would interfere with effective gelation of the hydrogel. The amount of the additive used depends on the particular application and may be readily determined by one skilled in the art using routine experimentation. For example, the solution may optionally include at least one pH modifier to adjust the pH of the solution. Suitable pH modifiers are well known in the art. The pH modifier may be an acidic or basic compound. Examples of acidic pH modifiers include, but are not limited to, carboxylic acids, inorganic acids, and sulfonic acids. Examples of basic pH modifiers include, but are not limited to, hydroxides, alkoxides, nitrogen-containing compounds other than primary and secondary amines, and basic carbonates and phosphates.

The aqueous solution comprising the oxidized polysaccharide may optionally include at least one thickener. The thickener may be selected from among known viscosity modifiers, including, but not limited to, polysaccharides and derivatives thereof, such as starch or hydroxyethyl cellulose.

The aqueous solution comprising the oxidized polysaccharide may optionally include at least one antimicrobial agent. Suitable antimicrobial preservatives are well known in the art. Examples of suitable antimicrobials include, but are not limited to, alkyl parabens, such as methylparaben, ethylparaben, propylparaben, and butylparaben; triclosan; chlorhexidine; cresol; chlorocresol; hydroquinone; sodium benzoate; and potassium benzoate. In one embodiment, the antimicrobial is triclosan.

The aqueous solution comprising the oxidized polysaccharide may also optionally include at least one colorant to enhance the visibility of the solution. Suitable colorants include dyes, pigments, and natural coloring agents. Examples of suitable colorants include, but are not limited to, FD&C and D&C colorants, such as FD&C Violet No. 2, D&C Green No. 6, D&C Green No. 5, D&C Violet No. 2, FD&C Yellow No. 6, FD&C Red No. 3; and natural colorants, such as beetroot red, canthaxanthin, chlorophyll, eosin, saffron, and carmine. In one embodiment, the colorant is FD&C Violet No. 2, D&C Green No. 6, D&C Green No. 5, or D&C Violet No. 2.

The aqueous solution comprising the oxidized polysaccharide may also optionally include at least one surfactant. Surfactant, as used herein, refers to a compound that lowers the surface tension of water. The surfactant may be an ionic surfactant, such as sodium lauryl sulfate, or a neutral surfactant, such as polyoxyethylene ethers, polyoxyethylene esters, and polyoxyethylene sorbitan.

Additionally, the aqueous solution comprising the oxidized polysaccharide may optionally include anti-inflammatory agents, such as indomethacin, salicylic acid acetate, ibuprophen, sulindac, piroxicam, and naproxen; thrombogenic agents, such as thrombin, fibrinogen, homocysteine, and estramustine; and radio-opaque compounds, such as barium sulfate and gold particles.

Multi-Arm Polyether Amines:

The multi-arm polyether amines are water-dispersible polyethers having the repeat unit [—O—R]—, wherein R is an hydrocarbylene group having 2 to 5 carbon atoms. The term "hydrocarbylene group" refers to a divalent group formed by removing two hydrogen atoms, one from each of two different carbon atoms, from a hydrocarbon. The multi-arm polyether amines of the invention include, but are not limited to, dendritic, comb, and star polyethers wherein at least three of the arms are terminated by a primary amine group. The multi-arm polyether amines have a molecular weight of about 450 to about 200,000 Daltons, in addition from about 2,000 to about 40,000 Daltons. Suitable examples of water-dispersible, multi-arm polyether amines include, but are not limited to, amino-terminated star, dendritic, or comb polyethylene oxides; amino-terminated star, dendritic or comb polypropylene oxides; amino-terminated star, dendritic or comb polyethylene oxide-polypropylene oxide copolymers; amino-terminated dendritic polyamidoamines, sold under the trade name Starburst® Dendrimers (available from Sigma-Aldrich, St Louis, Mo.); and polyoxyalkylene triamines, sold under the trade name Jeffamine®triamines, by Huntsman LLC. (Houston, Tex.). Examples of star polyethylene oxide amines, include, but are not limited to, various multi-arm polyethylene glycol amines, available from Nektar Transforming Therapeutics (Huntsville, Ala.), and star polyethylene glycols having 3, 4, or 8 arms terminated with primary amines (referred to herein as 3, 4 or 8-arm star PEG amines, respectively). The 8-arm star PEG amine is available from Nektar Transforming Therapeutics. Examples of suitable Jeffamine® triamines include, but are not limited to, Jeffamine® T-403 (CAS No. 39423-51-3), Jeffamine® T-3000 (CAS No. 64852-22-8), and Jeffamine® T-5000 (CAS No. 64852-22-8). In one embodiment, the water-dispersible multi-arm polyether amine is an eight-arm polyethylene glycol having eight arms terminated by a primary amine group and having a molecular weight of 10,000 Daltons (available from Nektar Transforming Therapeutics).

These multi-arm polyether amines are either available commercially, as noted above, or may be prepared using methods known in the art. For example, multi-arm polyethylene glycols, wherein at least three of the arms are terminated by a primary amine group, may be prepared by putting amine ends on multi-arm polyethylene glycols (e.g., 3, 4 and 8-arm star polyethylene glycols, available from Nektar Transforming Therapeutics) using the method described by Buckmann et al. (*Makromol. Chem.* 182:1379-1384, 1981). In that method, the multi-arm polyethylene glycol is reacted with thionyl bromide to convert the hydroxyl groups to bromines, which are then converted to amines by reaction with ammonia at 100° C. The method is broadly applicable to the preparation of other multi-arm polyether amines. Other methods that may used for preparing multi-arm polyether amines are described by Merrill et al. in U.S. Pat. No. 5,830,986, and by Chang et al. in WO 97/30103.

It should be recognized that the multi-arm polyether amines are generally a heterogeneous mixture having a distribution of species with different numbers of arms. However, there will be a predominant species that has a specific number of arms. For example, the 8-arm star PEG amine comprises a mixture of multi-arm star PEG amines, some having less than and some having more than 8-arms, but the predominant species is the 8-arm star PEG amine.

One factor to consider when selecting the optimum multi-arm polyether amine to be used for a given application is the degradation rate desired for the resulting hydrogel. It was discovered that the degradation rate of the hydrogel is dependent on the number of arms on the multi-arm polyether amine used to prepare the hydrogel. Specifically, the degradation rate of the hydrogel decreases as the number of arms on the multi-arm polyether amine is increased. Therefore, for applications in which a fast degradation rate is desired, a multi-arm polyether amine having 3 or 4 arms should be chosen, while in applications requiring a slow degradation rate, a multi-arm polyether amine having 6, 8 or more arms should be chosen.

In the invention, the multi-arm polyether amine is used in the form of an aqueous solution. The multi-arm polyether amine is added to water to give a concentration of about 5% to about 70% by weight, in addition from about 20% to about 50% by weight relative to the total weight of the solution. The optimal concentration to be used depends on the application and on the concentration of the oxidized polysaccharide used. In one embodiment, the concentrations of the oxidized polysaccharide and the multi-arm polyether amine are adjusted such that the aldehyde groups on the oxidized polysaccharide are in stoichiometric excess relative to the amine groups on the multi-arm polyether amine. In one embodiment, wherein an 8-arm star PEG amine is used as the multi-arm polyether amine, the amount of aldehyde groups is from about 1.1 times to about 50 times the amount of amine groups, in addition from about 3 times to about 15 times the amount of amine groups. In another embodiment wherein a Jeffamine® triamine is used as the multi-arm polyether amine, the amount of aldehyde groups is from about 0.5 times to about 3 times the amount of amine groups.

For use on living tissue, it is preferred that the aqueous solution comprising the multi-arm polyether amine be sterilized to prevent infection. Any of the methods described SUPRA for sterilizing the oxidized polysaccharide solution may be used.

The aqueous solution comprising the multi-arm polyether amine may further comprise various additives. Any of the additives described SUPRA for the oxidized polysaccharide solution may be used. Additionally, the solution may comprise a healing promoter, such as chitosan.

Additionally, the aqueous solution comprising the multi-arm polyether amine may optionally comprise at least one other multi-functional amine having one or more primary amine groups to provide other beneficial properties, such as hydrophobicity. The multi-functional amine may be a second water dispersible, multi-arm polyether amine, such as those described SUPRA, or another type of multi-functional amine, including, but not limited to, linear and branched diamines, such as diaminoalkanes, polyaminoalkanes, and spermine; branched polyamines, such as polyethylenimine; cyclic diamines, such as N,N'-bis(3-aminopropyl)piperazine, 5-amino-1,3,3-trimethylcyclohexanemethylamine, 1,3-bis(aminomethyl)cyclohexane, 1,4-diaminocyclohexane, and p-xylylenediamine; aminoalkyltrialkoxysilanes, such as 3-aminopropyltrimethoxysilane and 3-aminopropyltriethoxysilane; aminoalkyldialkoxyalkylsilanes, such as 3-aminopropyldiethoxymethylsilane, dihydrazides, such as adipic dihydrazide; linear polymeric diamines, such as linear polyethylenimine, α,ω-amino-terminated polyethers, α,ω-bis(3-aminopropyl)polybutanediol, β,ω-1-amino-terminated polyethers (linear Jeffamines®); comb polyamines, such as chitosan, polyallylamine, and polylysine, and di- and polyhydrazides, such as bis(carboxyhydrazido)polyethers and poly(carboxyhydrazido) star polyethers. Many of these compounds are commercially available from companies such as Sigma-Aldrich and Huntsman LLC. Typically, if present, the multi-functional amine is used at a concentration of about 5% by weight to about 1000% by weight relative to the weight of the multi-arm polyether amine in the aqueous solution.

In another embodiment, the multi-functional amine is provided in a separate solution at a concentration of about 5% by weight to about 100% by weight relative to the total weight of the solution. If the multi-functional amine is not used neat (i.e., 100% by weight), it is used in the form of an aqueous solution. For use on living tissue, it is preferred that the solution comprising the multi-functional amine be sterilized. Any of the methods described SUPRA for sterilizing the oxidized polysaccharide solution may be used. The aqueous solution comprising the multi-functional amine may further comprise various additives. Any of the additives described SUPRA for the oxidized polysaccharide solution or the multi-arm polyether amine solution may be used.

In one embodiment, the invention provides a kit comprising an aqueous solution comprising an oxidized polysaccharide and an aqueous solution comprising a multi-arm polyether amine. Each of the aqueous solutions may be contained in any suitable vessel, such as a vial or a syringe barrel.

In another embodiment, the invention provides a kit comprising an aqueous solution comprising an oxidized polysaccharide, an aqueous solution comprising a multi-arm polyether amine, and a third solution comprising a multi-functional amine, as described SUPRA. Each of the solutions may be contained in any suitable vessel, such as a vial or a syringe barrel.

Method of Application:

The aqueous solution comprising the oxidized polysaccharide and the aqueous solution comprising the multi-arm polyether amine may be applied to an anatomical site on tissue of a living organism in any number of ways. Once both solutions are applied to a site, they crosslink to form a hydrogel, a process referred to herein as curing, typically in about 2 seconds to about 2 minutes. Because the aldehyde groups on the oxidized polysaccharide may also covalently bind to amine groups on the tissue, the tissue adhesive of the invention is capable of covalently binding to tissue, thereby increasing its adhesive strength.

In one embodiment, the two aqueous solutions are applied to the site sequentially using any suitable means including, but not limited to, spraying, brushing with a cotton swab or brush, or extrusion using a pipet, or a syringe. The solutions may be applied in any order. Then, the solutions are mixed on the site using any suitable device, such as a cotton swab, a spatula, or the tip of the pipet or syringe.

In another embodiment, the two aqueous solutions are mixed manually before application to the site. The resulting mixture is then applied to the site before it completely cures using a suitable applicator, as described above.

In another embodiment, the two aqueous solutions are contained in a double-barrel syringe. In this way the two aqueous solutions are applied simultaneously to the site with the syringe. Suitable double-barrel syringe applicators are known in the art. For example, Redi describes several suitable applicators for use in the invention in U.S. Pat. No. 6,620,125, (particularly FIGS. 1, 5, and 6, which are described in Columns 4, line 10 through column 6, line 47) which is incorporated herein by reference. Additionally, the double barrel syringe may contain a motionless mixer, such as that available from ConProTec, Inc. (Salem, N.H.), at the tip to effect mixing of the two aqueous solutions prior to application.

In another embodiment wherein the optional third solution comprising a multi-functional amine is used, the three solutions are applied to the anatomical site in any order using any of the methods described SUPRA. In this embodiment, the double-barrel syringe may be modified to have three barrels, one for each of the solutions.

In another embodiment, the tissue adhesive of the invention is used to bond at least two anatomical sites together. In this embodiment, the aqueous solution comprising the oxidized polysaccharide is applied to at least one anatomical site, and the aqueous solution comprising the multi-arm polyether amine is applied to at least one of either the same site or one other site. The two or more sites are contacted and held together manually or using some other means, such as a surgical clamp, for a time sufficient for the mixture to cure, typically from about 2 seconds to about 2 minutes. Alternatively, a mixture of the two aqueous solutions either premixed manually or using a double-barrel syringe applicator, is applied to at least one of the anatomical sites to be bonded. The two or more sites are contacted and held together manually or using some other means, such as a surgical clamp, for a time sufficient for the mixture to cure.

In another embodiment wherein the optional third solution comprising a multi-functional amine is used along with the aqueous solution comprising the oxidized polysaccharide and the aqueous solution comprising the multi-arm polyether amine to bond at least two anatomical sites together, each of the three solutions is applied to at least one anatomical site in any order. The solutions may be applied to the same site or to different sites. Alternatively, the three solutions are premixed using any of the methods described SUPRA, and the resulting mixture is applied to at least one of the anatomical sites to be bonded before the mixture completely cures. The two or more sites are then contacted and held together manually or using some other means, such as a surgical clamp, for a time sufficient for the mixture to cure Medical and Veterinary Applications:

The tissue adhesive of the invention has many potential medical and veterinary applications, including, but not limited to, topical wound closure, surgical procedures, such as intestinal anastomosis, vascular anastomosis, and ophthalmic procedures; drug delivery, anti-adhesive applications, and as a bulking agent to treat urinary incontinence. For these uses, procedures involving the application of two aqueous solutions, one comprising the oxidized polysaccharide and the other comprising the multi-arm polyether amine are described below. The application of three solutions, wherein the third solution comprises an additional multi-functional amine, may also be used for these purposes using the procedures describe SUPRA.

The tissue adhesive of the invention may be used for treatment of topical wounds, including but not limited to, minor cuts, scrapes, irritations, abrasions, lacerations, burns, sores, and surgical wounds. For topical wound closure, the aqueous solution comprising the oxidized polysaccharide and the aqueous solution comprising the multi-arm polyether amine are applied to the wound using the methods described SUPRA, and the mixture is allowed to cure.

The tissue adhesive of the invention may also be used in surgical procedures, including but not limited to intestinal anastomosis, vascular anastomosis, and ophthalmic procedures, such as sealing corneal cataract incisions.

Intestinal anastomosis is a surgical procedure that is well known to skilled surgeons. The procedure, which involves joining two segments of the intestine together after a resection, is described by Sweeney et al. (*Surgery* 131:185-189, 2002). The two segments of the intestine are joined together using sutures or staples. A problem encountered with this procedure is leakage around the sutures or staples. Leakage rates of 5-8% have been reported (Bruce et al. *Br. J. Surg.* 88:1157-1168, 2001). The tissue adhesive of the invention may be used to supplement the sutures or staples used in intestinal anastomoses, providing a better seal that reduces leakage. In this application, the aqueous solution comprising the oxidized polysaccharide and the aqueous solution comprising the multi-arm polyether amine are applied to the intestine around the sutures or staples, using the methods described SUPRA, and the mixture is allowed to cure.

Additionally, the tissue adhesive of the invention may be used in vascular anastomosis procedures. This procedure is similar to intestinal anastomosis, described above, and is used for vascular grafts. The two segments of the blood vessel are joined together using sutures or staples. The tissue adhesive of the invention may be used to supplement the sutures or staples, providing a better seal that reduces leakage. In this application, the aqueous solution comprising the oxidized polysaccharide and the aqueous solution comprising the multi-arm polyether amine are applied to the blood vessel around the sutures or staples, using the methods described SUPRA, and the mixture is allowed to cure.

Temporal clear corneal incisions and scleral tunnel incisions are used during cataract surgery. These procedures are well known to the skilled cataract surgeon. Although these incisions can be sealed with sutures, many surgeons prefer sutureless, self-sealing incisions. However, problems arise with leakage through the sutureless incisions, causing endophthalmitis (Sarayba et al. Amer. *J. Opthamol.* 138:206-210, 2004, and Kim et al. *J. Cataract Refract Surg.* 21:320-325, 1995). The tissue adhesive of the invention may be used to seal both clear corneal incisions and scleral tunnel incisions to prevent leakage. In this application, the aqueous solution comprising the oxidized polysaccharide and the aqueous solution comprising the multi-arm polyether amine are applied to the site of the incision in the eye, using the methods described SUPRA, and the mixture is allowed to cure. Additionally, the two aqueous solutions may be coated on the sides of the scalpel blade used to make the incision, one solution on each side of the blade, to apply them to the site when the site is ready for closure.

The tissue adhesive of the invention may also be used to prevent adhesions between adjacent anatomical sites following surgery or injury to internal organs. The aqueous solution comprising the oxidized polysaccharide and the aqueous solution comprising the multi-arm polyether amine are applied to one anatomical site using the methods described SUPRA. The first site is prevented from contacting any adjacent site manually or using some other means, such as a surgical clamp, until the mixture cures, typically from about 2 seconds to about 2 minutes. After curing, the hydrogel is no longer adhesive, and serves as a barrier preventing adhesions of adjacent sites.

The tissue adhesive of the invention may also be used for drug delivery to a selected anatomical site. In this application, at least one of the aqueous solutions further comprises a pharmaceutical drug or therapeutic agent. Suitable pharmaceutical drugs and therapeutic agents are well known in the art. An extensive list is given by Kabonov et al. in U.S. Pat. No. 6,696,089, which is incorporated herein by reference (in particular, columns 16 to 18). Examples include, but are not limited to, antibacterial agents, antiviral agents, antifungal agents, anti-cancer agents, vaccines, radiolabels, anti-inflammatories, anti-glaucomic agents, local anesthetics, anti-neoplastic agents, antibodies, hormones, and the like. In this application, the aqueous solution comprising the oxidized polysaccharide and the aqueous solution comprising the multi-arm polyether amine, at least one of which further comprises the pharmaceutical drug or therapeutic agent of interest, are applied to the desired anatomical site using the methods described SUPRA. After the hydrogel cures, the drug or therapeutic agent is released to the desired anatomical site. The rate of release depends on the crosslink density of the hydrogel, which can be controlled by the extent of crosslinking, which in turn is determined by the concentrations of the oxidized polysaccharide and the polyfunctional polyether used, as well as the relative levels of functional groups present on these respective reactants. The concentration of reagents needed to obtain the proper rate of drug release for any particular application can be readily determined by one skilled in the art using routine experimentation.

The tissue adhesive of the invention may also be used as a bulking agent to treat urinary incontinence, particularly, female stress urinary incontinence. Stress urinary incontinence is the loss of urine from the bladder caused by pressure occurring during exercise, coughing, sneezing, etc. One cause of this problem is the weakening of the urethral sphincter, a ring-shaped muscle at the base of the bladder that controls the flow of urine. One remedy for this condition is to use a bulking agent to provide physical support to the urethral sphincter. In this application, the aqueous solution comprising the oxidized polysaccharide and the aqueous solution comprising the multi-arm polyether amine are applied to the tissue surrounding the sphincter, using the methods described SUPRA, preferably a mixture of the two aqueous solutions is injected using a standard cytoscope. The mixture cures into a firm, but pliable hydrogel. The increased bulk at the injection site provides the sphincter muscles with additional capability to control urine flow.

Additionally, the tissue adhesive of the invention may be useful for other medical applications. These applications include, but are not limited to, an adhesive to hold an implant in place, an adhesive used on tissue to block air, moisture, fluid or microbial migration, and an adhesive to replace or supplement sutures or staples in other surgical procedures, such as cholecystectomy, ostomy port, appendectomy, bariatrics, retinal reattachment, Cesarean closure, abdominal hysterectomy, and the closure of trauma punctures, and ruptured membranes.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "sec" means second(s), "d" means day(s), "mL" means milliliter(s), "L" means liter (s), "µL" means microliter(s), "cm" means centimeter(s), "mm" means millimeter(s), "rpm" means micrometer(s), "mol" means mole(s), "mmol" means millimole(s), "g" means gram(s), "mg" means milligram(s), "meq" means milliequivalent(s), "eq wt" means equivalent weight, "MW" means molecular weight, "M" means molar concentration, "wt %" means percent by weight, "PEG" means polyethylene glycol, "Dex" means oxidized dextran, "Vol" means volume, "na" means not applicable, "nd" means not determined, "Ox" means oxidation, "rpm" means revolutions per minute, and "kGy" means kilogray.

General Methods:
Reagents:

Dextran (MW=10,000) was purchased from Sigma-Aldrich (St Louis, Mo.). The 8-arm PEG amine (MW=10,000), having eight arms terminated by a primary amine group was purchased from Nektar Transforming Therapeutic (Huntsville, Ala.). Jeffamine T3000 and Jeffamine T403 were obtained from Huntsman LLC. (Houston, Tex.). Sodium periodate (99% purity, CAS No. 7790-28-5) was purchased from Acros Organics (Morris Plains, N.J.). All other reagents were obtained from Sigma-Aldrich unless otherwise noted.

Preparation of Oxidized Dextran:

The following procedure was used to prepare an oxidized dextran with about 48% aldehyde content conversion from dextran having a molecular weight of 10,000 Daltons. Similar procedures were used for dextrans having molecular weights of 40,000, 60,000, and 250,000 Daltons. Other aldehyde conversions were obtained by varying the concentration of the periodate solution used, as noted below.

Dextran (18.9 g) was added to 170.1 g of distilled water (to give a 10 wt % aqueous solution) in a 500 mL round bottom flask. The solution was stirred for 15 to 30 min. Then, 17.6 g of NaIO$_4$ in 158.4 g of distilled water (10-wt % aqueous solution) was added to the dextran solution. The concentration of the periodate solution may be varied depending on the aldehyde conversion desired. The mixture was stirred at room temperature for 5 h. After this time, the solution was removed from the round bottom flask, divided into four equal volumes and dispensed into 4 dialysis membrane tubes (MEMBRA-CEL™ Dialysis Tubing, molecular weight cut-off of 3500 Daltons, obtained from Viskase Companies, Inc., Willowbrook, Ill.). For dextran having a molecular weight of 40,000, 60,000, and 250,000 Daltons, a 14,000 Dalton cut-off dialysis membrane tube (Viskase Companies, Inc.) was used. The dialysis tubes were inserted into a 5 L flask containing 4.5 L of distilled water and dialyzed for up to 4 days. During this dialysis, the distilled water was changed after 2 days. The samples were removed from the dialysis membrane tubes and placed into a lyophilizer container. The samples were frozen using liquid nitrogen and placed into a lyophilyzer for 24 to 48 h or until all the water was evaporated.

The dialdehyde content in the resulting oxidized dextran was determined using the following procedure. The oxidized dextran (0.1250 g) was added to 10 mL of 0.25 M NaOH in a 250 mL Erlenmeyer flask. The mixture was gently swirled and then placed in a temperature-controlled sonicator bath at 40° C. for 5 min until all the material dissolved, giving a dark yellow solution. The sample was removed from the bath and immediately cooled under cold tap water for 5 min. Then, 15.00 mL of 0.25 M HCl was added to the solution, followed by the addition of 50 mL of distilled water and 1 mL of 0.2% phenolphthalein solution. This solution was titrated with 0.25 M NaOH using a 50 mL buret and the endpoint was determined by a color change from yellow to purple/violet.

The dialdehyde content, also referred to herein as the oxidation conversion, in the oxidized dextran sample was calculated using the following formula:

$$\text{Dialdehyde Content} = \frac{(Vb-Va)_s}{W_s/M} - \frac{(Vb-Va)_p}{W_p/M} \times 100(\%)$$

Vb=total meq of base
Va=total of meq of acid
W=dry sample weight (mg)
M=molecular weight of repeating unit=162
S=the oxidized sample
P=the original sample Examples 1-16

In-Vitro Burst Testin of a Sealed Scalpel Incision

The purpose of these Examples was to demonstrate the burst strength of a seal made with various tissue adhesives of an incision made in swine uterine horn.

In these Examples, a syringe pump system was used to measure the burst strength of a seal of an incision made in a section of swine uterine horn. The syringe pump (Model No. 22, Harvard Apparatus, Holliston, Mass.) was modified to be equipped with two 30 mL syringes, which were connected together through a "Y" junction. Water was pumped through a single piece of Tygon® R-36 tubing (0.6 cm diameter) and through a pressure gauge (Model PDG 5000L, Omega Engineering, Stamford, Conn.).

An approximately 12.5 cm section of clean swine uterine horn, obtained from a local abattoir, was fitted on one end with a metal plug with a feed line fitting for water feed from the syringe pump and on the other end with a metal plug with a threaded hole which could be sealed with a machine screw. The plugs were held in place with nylon ties around the outside of the uterine horn. An incision was made through the uterine horn wall into the interior by puncturing with a Bard Parker™ surgical blade handle 5 (obtained from BD Surgical Products, Franklin Lakes, N.J.), fitted with a #15 surgical blade. The incision on the outside of the uterine horn was wider than the scalpel blade (typically 4-5 mm) while the hole through the inside wall was about 3 mm (about equal to the blade). This size incision mimics the distance between the interrupted sutures if an intestine were to be cut and later sutured. The uterine horn was filled with water containing a purple dye via the syringe pump until water began to leak from the open hole in the end plug and also from the scalpel puncture in the uterine horn wall. The pump was then turned off and the end plug was sealed with the machine screw. The scalpel incision site was blotted dry using a paper towel.

The oxidized dextran solutions and the multi-arm polyether amine solutions were prepared in water. The two solutions were applied to the incision using either of two methods. In one method, the solutions were applied to the site using a micropipet (Eppendorf®, Brinkmann Instruments, Inc., Westbury, N.Y.) and the solutions were mixed on the surface using a spatula. After the application, the adhesive was allowed to cure at room temperature for no longer than 2 min. In the second application method, two 1 mL syringes were fitted with a "Y" connector (obtained from Micromedics, Inc., St. Paul, Minn.). A Kenics type motionless mixer (obtained from ConProTec, Inc., Salem, N.H.) was inserted at the end of the "Y" connector. The internal diameter of the mixer was about 3 mm and the length was 48 mm with 17 mixing steps. The end buttons of the two syringe plungers were held in register by means of a yoke plate, allowing them to be depressed simultaneously, thereby depositing the desired quantity of the adhesive, with the correct proportion of the two solutions, onto the site of the incision.

In these Examples, dextran having different molecular weights, different oxidation conversions, and different concentrations were used, as shown in Table 1. The multi-arm polyether amines used were 8-arm PEG amine, Jeffamine T3000, and Jeffamine T403. The 8-arm PEG amine was used at different concentrations and the ratio of the volume of dextran solution to amine solution was varied, as shown in Table 1.

For comparison, a commercial Fibrin adhesive (obtained from Baxter Healthcare Corp., Deerfield, Ill.) was used to seal the incision in swine uterine horn and the burst pressure was measured. The Fibrin adhesive was prepared and used according to the manufacture's instructions.

Burst pressure testing, also referred to herein as leak pressure testing, was done by pressurizing the sealed uterine horn with water from the syringe pump at a flow rate of 11 mL/min until the bioadhesive seal began to leak, at which point the pressure was recorded. Adhesive failure was attributed when the water leaked under the seal between the hydrogel and the tissue surface. Cohesive failure was attributed when the water penetrated and leaked through the hydrogel itself. Burst pressure testing was also done on the unsealed uterine horn and the leak pressure was <10 mm of mercury (Hg). The results of the burst testing are summarized in Table 1.

The results of these Examples indicate that as the oxidation conversion of the polysaccharide increases, the leak pressure increases, thereby, providing a stronger seal. However, with relatively high oxidation conversions (i.e., greater than about 60%), the adhesive crosslinks very rapidly and does not have sufficient time to spread and react with the tissue. Generally, the leak pressures increased with increasing concentration of the oxidized dextran between 10% and 30% by weight. Additionally, high leak pressures were obtained using 8-arm PEG amine concentrations of 10 to 70% by weight. In almost all of these Examples, the leak pressure obtained with the tissue adhesives of the invention was significantly higher than that obtained with the Fibrin adhesive. For leak pressures below 100 mm of mercury, the failure was cohesive, while for leak pressures above 100 mm of mercury, the failures were interfacial (i.e., adhesive failure).

TABLE 1

Results of In Vitro Burst Testing of a Sealed Incision in Swine Uterine Horn

| Example | Dex MW | Dex Ox (%) | Dex Eq Wt | Dex wt % | Amine | Amine wt % | Dex Vol (µL) | Amine Vol (µL) | Leak mm Hg |
|---|---|---|---|---|---|---|---|---|---|
| 1 | 10,000 | 20 | 389 | 30 | 8-arm PEG | 50 | 30 | 30 | 135 |
| 2 | 10,000 | 46 | 160 | 30 | 8-arm PEG | 50 | 30 | 30 | 150 |
| 3 | 10,000 | 46 | 160 | 30 | 8-arm PEG | 50 | 64 | 8 | 150 |
| 4 | 10,000 | 46 | 160 | 30 | 8-arm PEG | 50 | 40 | 20 | 135 |
| 5 | 10,000 | 46 | 160 | 30 | 8-arm PEG | 50 | 20 | 40 | 85 |
| 6 | 10,000 | 46 | 160 | 10 | 8-arm PEG | 50 | 30 | 30 | 85 |
| 7 | 10,000 | 46 | 160 | 20 | 8-arm PEG | 50 | 30 | 30 | 100 |
| 8 | 40,000 | 15 | 525 | 30 | 8-arm PEG | 50 | 30 | 30 | 15 |
| 9 | 40,000 | 74 | 95 | 30 | 8-arm PEG | 50 | 30 | 30 | 60 |
| 10 | 60,000 | 19 | 410 | 30 | 8-arm PEG | 50 | 30 | 30 | 110 |
| 11 | 250,000 | 6 | 1335 | 30 | 8-arm PEG | 50 | 30 | 30 | 175 |
| 12 | 10,000 | 46 | 160 | 25 | 8-arm PEG | 10 | 30 | 30 | 50 |
| 13 | 10,000 | 46 | 160 | 25 | 8-arm PEG | 70 | 30 | 30 | 140 |
| 14 | 10,000 | 46 | 160 | 30 | Jeffamine | neat | 30 | 30 | 60 |

TABLE 1-continued

Results of In Vitro Burst Testing of a Sealed Incision in Swine Uterine Horn

| Example | Dex MW | Dex Ox (%) | Dex Eq Wt | Dex wt % | Amine | Amine wt % | Dex Vol (μL) | Amine Vol (μL) | Leak mm Hg |
|---|---|---|---|---|---|---|---|---|---|
| 15 | 10,000 | 46 | 160 | 30 | T3000 Jeffamine T403 | neat | 40 | 20 | 30 |
| 16 Comparative, Fibrin | na | na | na | na | na | na | na | na | 15 mm |

Example 17

In-Vitro Burst Testing of a Sealed Scalpel Incision Using a Two Amine System

The purpose of this Example was to demonstrate the burst strength of a seal, made with a two-amine based tissue adhesive, of an incision made in swine uterine horn.

The procedures used in this Example are the same as those described in Examples 1-16, except that two different amines were used to react with the oxidized dextran. The dextran had a molecular weight of 10,000, and the oxidization conversion was 46% (eq wt of 160). The dextran solution had a concentration of 30 wt %. The first amine solution contained the 8-arm PEG amine at a concentration of 50 wt % and the second amine solution was neat liquid Jeffamine T403 (i.e., 100 wt %). The solutions were applied to the site using a micropipet (Eppendorf®) to deliver 40 μL of the oxidized dextran solution, 20 μL of the 8-arm PEG amine solution, and 12 μL of the Jeffamine. The solutions were mixed on the site using a spatula. The burst strength was determined as described in Examples 1-16. A leak pressure of 125 mm of mercury was obtained. This result demonstrates that an effective tissue adhesive was formed by reacting oxidized dextran with two different multi-arm polyether amines.

Examples 18-23

In-Vitro Burst Testing of a Sealed Sutured Enterotomy Incision in Swine Uterine Horn The purpose of these Examples was to demonstrate the burst strength of a sutured enterotomy incision in swine uterine horn that was sealed with various tissue adhesives.

A scalpel incision was made around one-half the circumference of an approximately 12.5 cm section of clean, fresh swine uterine horn. This incision was then closed with 2-3 interrupted sutures using 5-0 Vicryl suture line (Ethicon Inc., Summerville, N.J.). The everted suture technique was used, in which only the outer layer of tissue was drawn together. The sutured uterine horn was fitted on one end with a metal nozzle with a feed line for water from a syringe pump and clamped on the other end with a hemostat. The nozzle was held in place with a nylon tie. The suture line was blotted with a paper towel and then the adhesive was applied over the sutures using the methods described in Examples 1-16.

The components of the tissue adhesives used in these Examples were an aqueous solution of oxidized dextran (MW of 10,000), 46% to 48% oxidation conversion, having a concentration of 25 or 30 wt % and an aqueous solution of 8-arm PEG amine, having a concentration of 20 to 50 wt %. The ratio of the volumes of the two solutions used was varied, as shown in Table 2. The Fibrin adhesive described in Examples 1-16 was used for comparison.

Burst pressure testing was done as described in Examples 1-16. The sutured uterine horn before sealing was also tested and the leak pressure was 10 mm of mercury. The results of the burst pressure testing are given in Table 2.

TABLE 2

Results of In Vitro Burst Testing of a Sutured Enterotomy Incision in Swine Uterine Horn

| Example | Dex MW | Dex Ox (%) | Dex Eq Wt | Dex wt % | 8-arm PEG Amine wt % | Dex Vol (μL) | Amine Vol (μL) | Leak mm Hg |
|---|---|---|---|---|---|---|---|---|
| 18 | 10,000 | 46 | 160 | 30 | 50 | 40 | 10 | 120 |
| 19 | 10,000 | 46 | 160 | 30 | 50 | 30 | 30 | 110 |
| 20 | 10,000 | 46 | 160 | 30 | 50 | 20 | 40 | 85 |
| 21 | 10,000 | 48 | 167 | 25 | 20 | 50 | 50 | 275 |
| 22 | 10,000 | 48 | 167 | 25 | 25 | 50 | 50 | 200 |
| 23, Comparative, Fibrin | na | na | na | na | na | na | na | 25 |

These results demonstrate that an effective seal of a sutured enterotomy incision in swine uterine horn was obtained using the tissue adhesives of the invention. Generally, as the ratio of the 8-arm PEG amine to dextran was increased, the resulting adhesive became softer and had poorer mechanical properties. In all these Examples, the leak pressure obtained with the tissue adhesives of the invention was significantly higher than that obtained with the Fibrin adhesive. For leak pressures below 100 mm of mercury, the failure was cohesive, while for leak pressures above 100 mm of mercury, the failures were interfacial (i.e., adhesive failure).

Examples 24-27

In-Vitro Burst Testing of a Sealed Sutured Incision in Swine Uterine Horn

The purpose of these Examples was to demonstrate the burst strength of a sutured incision in swine uterine horn that was sealed with various tissue adhesives.

A scalpel incision was made around the full circumference of an approximately 12.5 cm section of clean swine uterine horn. This incision was then closed with interrupted sutures using 5-0 Vicryl suture line. The inverted suturing technique was used, in which just the inner layer of the muscle was drawn together. This is the preferred technique used in human intestinal anastomosis procedures. The sutured uterine horn was fitted on one end with a metal nozzle with a feed line for water from a syringe pump and clamped on the other end with a hemostat. The nozzle was held in place with a nylon tie. The suture line was blotted with a paper towel and then the adhesive was applied over the sutures, as described in Examples 1-16.

The components of the tissue adhesives used in these Examples were an aqueous solution of oxidized dextran (MW of 10,000), 46% oxidation conversion, having varying concentrations and an aqueous solution of 8-arm PEG amine, having varying concentrations, as shown in Table 3. The Fibrin adhesive described in Examples 1-16 was used for comparison.

Burst pressure testing was done as described in Examples 1-16. The sutured uterine horn before sealing was also tested and the leak pressure was 10 mm of mercury. The results of the burst pressure testing are given in Table 3.

TABLE 3

Results of In Vitro Burst Testing of a Sutured Incision in Swine Uterine Horn

| Example | Dex MW | Dex Ox (%) | Dex Eq Wt | Dex wt % | 8-arm PEG Amine wt % | Dex Vol (μL) | Amine Vol (μL) | Leak mm Hg |
|---|---|---|---|---|---|---|---|---|
| 24 | 10,000 | 46 | 160 | 20 | 20 | 250 | 250 | 105 |
| 25 | 10,000 | 46 | 160 | 10 | 50 | 250 | 250 | 105 |
| 26 | 10,000 | 46 | 160 | 30 | 50 | 250 | 250 | 125 |
| 27, Comparative, Fibrin | na | na | na | na | na | na | na | 25 |

These results demonstrate that an effective seal of a sutured incision in swine uterine horn was obtained using the tissue adhesives of the invention. In all these Examples, the leak pressure obtained for the tissue adhesives of the invention was significantly higher than that obtained with the Fibrin adhesive. For leak pressures below 100 mm of mercury, the failure was cohesive, while for leak pressures above 100 mm of mercury, the failures were interfacial (i.e., adhesive failure).

Examples 28-29

In-Vitro Burst Testing of a Sealed Incision in the Eye

The purpose of these Examples was to demonstrate the burst strength of a sealed incision in the eye from a New Zealand rabbit.

A 2-3 mm temporal clear corneal incision was made in the eye from a New Zealand rabbit (obtained from Covance Research Products, Denver, Pa.) to mimic the incision made for cataract surgery. A Bard Parker™ surgical blade handle 5 (obtained from BD Surgical Products, Franklin Lakes, N.J.), fitted with a #15 surgical blade was used to make the incision. The incision was sealed by applying the components of the tissue adhesive to the site, as described in Examples 1-16.

The components of the tissue adhesives used in these Examples were an aqueous solution of oxidized dextran (MW of 10,000), 46% oxidation conversion, having varying concentrations and an aqueous solution of 8-arm PEG amine, having varying concentrations, as shown in Table 4.

The eye was pressurized with water from the syringe pump at a flow rate 11 mL/min until leakage was detected at which point the pressure was recorded. Adhesive failure was attributed when the water leaked under the seal between the hydrogel and the tissue surface. Cohesive failure was attributed when the water penetrated and leaked through the hydrogel itself. The eye was tested before the incision was sealed and the leak pressure was <15 mm of mercury. The results of the burst pressure testing are summarized in Table 4.

TABLE 4

Results of In Vitro Burst Testing of a Sealed Incision in the Eye

| Example | Dex MW | Dex Ox (%) | Dex Eq Wt | Dex wt % | 8-arm PEG Amine wt % | Dex Vol (μL) | Amine Vol (μL) | Leak mm Hg |
|---|---|---|---|---|---|---|---|---|
| 28 | 10,000 | 46 | 160 | 25 | 50 | 10 | 10 | 235 |
| 29 | 10,000 | 46 | 160 | 27 | 50 | 5 | 5 | 250 |

These results demonstrate that an effective seal of a temporal clear corneal incision in the eye was obtained using the tissue adhesives of the invention. In both Examples, the leak was through the adhesive (i.e. cohesive failure).

Examples 30-37

In Vitro Degradation of Tissue Adhesives

The purpose of these Examples was to demonstrate the mechanical stability of the tissue adhesives of the invention in vitro.

The tissue adhesive samples were prepared by mixing aqueous solutions of the oxidized dextran and the multi-arm polyether amine. Dextran having a molecular weight of 10,000 was used in these Examples. The concentrations and the volumes of the two aqueous solutions used are given in Table 5.

After the adhesives cured, the samples were placed inside jars containing pH 7.4 phosphate buffer solution. The jars were placed inside a temperature-controlled shaker set at 80 rpm and 37° C. The samples were monitored for degradation (i.e., the disappearance of the material) by visual inspection, mechanical properties, as determined using a 45-degree bend test, and weight gain (measured after 24 h). The 45-degree bend test involved bending the adhesive to an angle of about 45 degrees and observing for cracking. If no cracking was observed, the material was deemed to have passed the test. The results are summarized in Table 5.

TABLE 5

Results of In Vitro Degradation of Tissue Adhesives

| Ex. | Dex Ox (%) | Dex Eq Wt | Dex wt % | Amine | Amine wt % | Dex Vol (μL) | Amine Vol (μL) | Degradation | 45-degree bend | Weight Gain (%) |
|---|---|---|---|---|---|---|---|---|---|---|
| 30 | 20 | 390 | 40 | 8-arm PEG | 50 | 30 | 30 | 24 h | yes | nd |
| 31 | 46 | 160 | 20 | 8-arm PEG | 50 | 10 | 50 | 3 h | yes | nd |

TABLE 5-continued

Results of In Vitro Degradation of Tissue Adhesives

| Ex. | Dex Ox (%) | Dex Eq Wt | Dex wt % | Amine | Amine wt % | Dex Vol (μL) | Amine Vol (μL) | Degradation | 45-degree bend | Weight Gain (%) |
|---|---|---|---|---|---|---|---|---|---|---|
| 32 | 46 | 160 | 20 | 8-arm PEG | 50 | 30 | 30 | 15 d | yes | 250 |
| 33 | 46 | 160 | 30 | 8-arm PEG | 50 | 30 | 30 | 15 d | yes | 250 |
| 34 | 46 | 160 | 30 | 8-arm PEG | 50 | 40 | 20 | 30 d | yes | 175 |
| 35 | 46 | 167 | 25 | 8-arm PEG | 20 | 50 | 50 | >10 d | yes | 115 |
| 36 | 46 | 167 | 25 | 8-arm PEG | 25 | 50 | 50 | >10 d | yes | 115 |
| 37 | 46 | 160 | 30 | Jeffamine T3000 | neat | 30 | 30 | >30 d | yes | 2 |

These results demonstrate that the tissue adhesives of the invention have good mechanical properties. The rate of degradation may be controlled by varying the degree of oxidation of the dextran, the concentrations of the polysaccharide and the multi-arm polyether amine, the volume ratio of the two aqueous solutions, and the multi-arm polyether amine used. The data also suggests that to reduce the swelling or increase the long-term mechanical properties of the tissue adhesive, a lower concentration of the 8-arm PEG amine may be beneficial, specifically 20 to 25 wt %.

Examples 38-39

In Vitro Degradation of Tissue Adhesives Prepared Using Two Amines

The purpose of these Examples was to demonstrate the mechanical stability of tissue adhesives prepared using two different multi-arm polyether amines in vitro.

The procedures used in these Examples were the same as those described in Examples 30-37. Dextran having a molecular weight of 10,000, and an oxidation conversion of 46% (eq wt of 160) was used in these Examples. The concentration of the aqueous dextran solution was 30 wt %. The first amine solution contained the 8-arm PEG amine at a concentration of 50 wt %. The second amine was either Jeffamine T3000 or Jeffamine T403, which were used neat, as indicated in Table 6. The volumes of the three solutions and the results are also given in Table 6.

TABLE 6

Results of In Vitro Degradation of Tissue Adhesives Prepared Using Two Amines

| Example | Dex Vol (μL) | Amine 1 Vol (μL) | Amine 2 | Amine 2 Vol (μL) | Degradation | 45-degree bend | Weight Gain (%) |
|---|---|---|---|---|---|---|---|
| 38 | 40 | 20 | Jeffamine T3000 | 4 | 25 d | yes | 180 |
| 39 | 40 | 12 | Jeffamine T403 | 10 | 12 d | no | 150 |

These results demonstrate that the tissue adhesives of the invention prepared using two different multi-arm amines have good mechanical properties.

Example 40

Sterilization of Tissue Adhesive Components and Delivery Devices

The purpose of this Example was to demonstrate the sterilization of the aqueous solution comprising oxidized dextran, the aqueous solution comprising the 8-arm PEG amine, and the components of a delivery device.

Aqueous solutions (20-30 wt %) of oxidized dextran and aqueous solutions (20-50 wt %) of 8-arm PEG amine were sterilized by gamma irradiation under a flux of 25 kGy ($2.5 \times 10^6$ rad). The solutions were contained in glass vials during irradiation. The solutions may also be contained in sealed, disposable syringes during irradiation.

The "Y" connectors of the delivery device (described in Examples 1-16), used to connect the two 1 mL syringes, were also sterilized by gamma irradiation under a flux of 25 kGy ($2.5 \times 10^6$ rad).

The motionless mixing tips of the delivery device were irradiated under a flux of 25 kGy ($2.5 \times 10^6$ rad). However, the tips became "yellowish" in color and broke due to brittleness, even under a minimal stress. The mixing tips were sterilized by autoclaving at 120° C. for 15 min without any ill effects.

The sterilized aqueous solutions were tested for gelation, and the resulting gels were tested for mechanical degradation and leak pressure, using the methods described in the previous Examples. The sterilized solutions were found to be very similar to the unsterilized solutions. These results demonstrate the ease of sterilization of the aqueous solutions and the delivery device.

Example 41

In Vitro Biocompatibility Testing

The purpose of this Example was to demonstrate the safety of the aqueous solutions comprising the oxidized dextran and the 8-arm PEG amine, and the dextran-PEG hydrogel that results from their reaction in an in vitro test.

The testing was done using Chinese hamster ovary (CHO-K1) cell cultures according to ISO10993-5:1999. The Chinese hamster ovary (CHO-K1) cells were obtained from the American Type Culture Collection (ATCC), Manassas, Va., and were grown in F12-K medium supplemented with 10% fetal bovine serum.

The Chinese hamster ovary (CHO-K1) cell culture was challenged with aqueous solutions (5, 10, 15, 20, 25, 27 and 30 wt %) of oxidized dextran (MW=10,000, 46% oxidation conversion, eq wt=160). The CHO-K1 cells were seeded in a culture plate at 55,000 cells per well and incubated with 1 mL of culture medium for 24 h. Then, 100 µL of oxidized dextran solution was added.

Similarly, a Chinese hamster ovary (CHO-K1) cell culture was challenged with aqueous solutions (10, 20, 30, 40, 50, 60 and 70 wt %) of 8-arm PEG amine (MW=10,000, eq wt=1250). The CHO-K1 cells were seeded in a culture plate at 55,000 cells per well and incubated with 1 mL of culture medium for 24 h. Then, 100 µL of the 8-arm PEG-amine solution was added.

Additionally, Chinese hamster ovary (CHO-K1) cell cultures were challenged with aqueous extracts of hydrogels made from combining (10, 15, 20, 25, 27 and 30 wt %) aqueous solutions of oxidized dextran (MW=10,000, 46% oxidation conversion, eq wt=160) with an aqueous solution of 8-arm PEG amine (MW=10,000, 50 wt %, eq wt=1250). The liquid extracts of the hydrogels were obtained by incubating the hydrogel with Dulbecco's modified essential medium (DMEM) at 37° C. for 24 h. The extracts were sterilized by ultrafiltration and then, serially diluted with DMEM. The CHO-K1 cells were seeded in a 96-well culture plate at 55,000 cells per well and incubated with culture medium for 24 h. Then, the DMEM was removed, and 100 µL of hydrogel extract was added to each well. The cytotoxicity was determined using the tetrazolium-based colorimetic assay (MTT), as described below, after 24 h of extract exposure.

The cytotoxicity was determined using the tetrazolium-based colorimetic assay (MTT), as described by Sgouras et al. (*Journal of Materials Science: Materials in Medicine* 1:61-68, 1990) and an ATP bioluminescence assay (Toxilight), as described by Crouch et al. (*Journal of Immunological Methods*

Example 42

In Vitro Biocompatibility Testing

The purpose of this Example was to demonstrate the safety of the dextran-PEG hydrogel in an in vitro test using NIH3T3 human fibroblast cell cultures.

The testing was done using NIH3T3 human fibroblast cell cultures according to ISO10993-5:1999. The NIH3T3 human fibroblast cells were obtained from ATCC and were grown in Dulbecco's modified essential medium (DMEM), supplemented with 10% fetal calf serum.

An NIH3T3 human fibroblast cell culture was challenged with hydrogels made by combining (10, 15, 20, 25, 27 and 30 wt %) aqueous solutions of oxidized dextran (MW=10,000, 46% oxidation conversion, eq wt=160) with an aqueous solution of the 8-arm PEG amine (MW=10,000, 50 wt %, eq wt=1250). The hydrogel was coated on the bottom of a well in a polystyrene culture plate such that about ¼ of the well bottom was covered. The well was then sterilized under UV light and seeded with 50,000-100,000 NIH3T3 cells. The cells grew normally confluent and coated the well bottom, growing up to the edges of the hydrogel; however, they did not overgrow the hydrogel. This result demonstrates a lack of cytotoxicity of the hydrogel, as well as the lack of adhesion of cell cultures to the hydrogel.

Example 43

In Vitro Biocompatibility Testing

The purpose of this Example was to demonstrate the non-inflammatory response produced by the dextran-PEG hydrogel in an in vitro test using J774 Macrophage.

The testing was done using J774 Macrophage cultures according to ISO10993-5:1999. The J774 Macrophage cells were obtained from ATCC and were grown in DMEM supplemented with 10% fetal bovine serum.

A J774 mouse peritoneal macrophage cell culture was challenged with a hydrogel made by combining (10, 15, 20, 25, 27 and 30 wt %) aqueous solutions of oxidized dextran (MW=10,000, 46% oxidation conversion, eq wt=160) with an aqueous solution of 8-arm PEG amine (MW=10,000, 50 wt %, eq wt=1250). The hydrogel was coated on the bottom of a well in a polystyrene culture plate such that about ¼ of the well bottom was covered. The well was then sterilized under UV light and seeded with J774 cells. The cell culture was then analyzed for TNF-α, an indicator of inflammatory response, using an ELISA assay, as described by Lara et al. (*Journal of Dental Research* 82(6):460-465, 2003). The TNF-α titer was similar to the negative control (a blank well), indicating the non-inflammatory nature of the hydrogels.

Example 44

In Vivo Biocompatibility Testing

The safety of the dextran-PEG hydrogels was further demonstrated by "painting" a patch of hydrogel onto the small intestine of living rabbits. The animals were closed and fed normally and then were sacrificed 3 days later. The intestinal and adjoining tissues under and around the hydrogel adhesive patch were examined for edema, erythema, toxicity, inflammation, degradation of the hydrogel, adhesion to the intestinal wall and lack of adhesion tissue growth.

Five white New Zealand rabbits (1 year old, approximately 4 kg in weight) were fasted overnight. Prior to surgery, the animals were treated with buprenorphine, then anaesthetized with a mixture of ketamine and xylazine. A standard laparotomy procedure was performed to isolate a section of the duodenum of the small intestine. A single "marker" stitch of blue-dyed polypropylene suture material (Prolene®, Ethicon) was placed in the duodenum in the outer layer of intestinal tissue about 10 cm distal from the stomach. This was done to aid in locating the hydrogel patch at necropsy. A patch of hydrogel about 1 cm×2 cm was applied to the duodenum about 12 cm distal from the stomach in the following manner. Using an micropipet (Eppendorf®) about 100 µL of oxidized dextran solution (30 wt %, 46% oxidation conversion, eq wt=160) was painted on the duodenum, followed by the application of 100 µL of 8-arm PEG amine solution (50 wt %, eq. wt=1250). The mixture was stirred vigorously on the site with a thin spatula for 2-5 sec or until the mixture began to gain noticeable viscosity. Within 15 sec the patch was tack free. The patch was allowed to cure for 2 min and then the peritoneum and abdomen were closed in layers using standard surgical procedure. The intestine surface was covered about 90% of the way around, leaving the mesentery uncovered.

At necropsy 3 days later, the adhesive application site was examined for gross tissue responses and the presence of the adhesive. The severity of erythema and edema were assessed using a scoring system that is consistent with the ISO intracutaneous reactivity test (ISO 10993-12). The examination revealed good adhesion of the hydrogel adhesive in all cases and no observable inflammation. There were no fibrous adhesions or attachment to adjacent tissue. There was swelling of the hydrogel, but no deterioration of the polymer coating. In all cases, intestinal peristalsis could easily move past the adhesive site. Following the gross examination, the tissue was excised and fixed in 4% formalin for histopathology analysis. The tissue samples were embedded, sectioned, and stained using standard methods. The histopathological analysis revealed the biocompatibility of the hydrogel.

Example 45

Comparative Example of In Vivo Biocompatibility Testing of Fibrin Adhesive

The purpose of this Example was to compare the performance of the Fibrin adhesive in the in vivo biocompatibility test with that of the dextran-PEG adhesive, as described in Example 44.

The procedure described in Example 44 was followed, except that the Fibrin adhesive (200 µL), prepared according to the manufacturer's instructions and applied with its delivery device, was painted on the duodenum. The patch was allowed to cure for 2 min and then the peritoneum and abdomen were closed in layers using standard surgical procedure. The intestine surface was covered about 90% of the way around, leaving the mesentery uncovered.

At necropsy 3 days later, the adhesive application site was examined for gross tissue responses and the presence of the adhesive. The severity of erythema and edema were assessed using a scoring system that is consistent with the ISO intracutaneous reactivity test (ISO 10993-12). The examination revealed poor adhesion. The adhesive patches had fallen off the site due to poor adhesion and there was no observable inflammation. There were no fibrous adhesions or attachment to adjacent tissue. In all cases, intestinal peristalsis could easily move past the adhesive site. Histopathological analysis of the site revealed very minor inflammatory response.

This result demonstrates the superior in vivo adhesion of the dextran-PEG adhesive, described in Example 44, compared to the Fibrin adhesive.

Example 46

Sealing a Rabbit Enterotomy In Vivo

The purpose of this Example was to demonstrate the safety and efficacy of the dextran-PEG adhesive in sealing around a suture line of an enterotomy incision in the small intestine of a living rabbit. After the application of the adhesive around the sutures and incision, it was allowed to cure. The animals were closed and fed normally and then were sacrificed 3 days later. The intestinal and adjoining tissues under and around the hydrogel adhesive patch were examined for edema, erythema, toxicity, inflammation, degradation of the hydrogel, adhesion to the intestinal wall and lack of adhesion tissue growth.

Five white New Zealand rabbits (1 year old, approximately 4 kg in weight) were fasted overnight. Prior to surgery, the animals were treated with buprenorphine, then anaesthetized with a mixture of ketamine and xylazine. A standard laparotomy procedure was performed to isolate a section of the duodenum of the small intestine. A single "marker" stitch of blue-dyed polypropylene suture material (Prolene®, Ethicon) was placed in the duodenum in the outer layer of intestinal tissue about 10 cm distal from the stomach. This was done to aid in locating the hydrogel patch at necropsy. A 5-mm incision was made about 12 cm distal from the stomach and the incision was closed with two 5-0 Vicryl sutures. A patch of hydrogel was applied to the small intestine over the stitches in the following manner. Using the delivery device described in Examples 1-16 with a motionless mixer having 8 mixing steps, 100 µL of oxidized dextran solution (30 wt %, 46% oxidation conversion, eq wt=160) mixed in with 100 µL of 8-arm PEG amine solution (50 wt %; eq wt=1250) was delivered to the enterotomy site. The adhesive clotted the noticeable bleeding in place and was able to crosslink and become tack free within 15 sec. The patch was allowed to cure for 2 min and then the peritoneum and abdomen were closed in layers using standard surgical procedure. The intestine surface was covered about 90% of the way around, leaving the mesentery uncovered.

At necropsy 3 days later, the adhesive application site was examined for gross tissue responses and the presence of the adhesive. The severity of erythema and edema were assessed using a scoring system that is consistent with the ISO intracutaneous reactivity test (ISO 10993-12). The examination revealed good adhesion of the hydrogel adhesive in all cases and no observable inflammation. There were no fibrous adhesions or attachment to adjacent tissue. There was swelling of the hydrogel, but no deterioration of the polymer coating. Following the gross examination, the tissue was excised and fixed in 4% formalin for histopathology analysis. The tissue samples were embedded, sectioned, and stained using standard methods. The histopathological analysis revealed the biocompatibility of the hydrogel.

Sections of about 12.5 cm of the intestine were excised from the rabbits and evaluated for leak pressure, as described in Examples 1-16. In all cases the leak pressure was at least 30 mm of mercury, indicating a good seal of the incision.

For comparison, rabbits were closed without the application of an adhesive. Necropsy 3 days later revealed gross adhesions at the site due to leakage. Histopathological evaluation revealed inflammatory response due to leakage at the site.

Example 47

Comparative Example of Sealing a Rabbit Enterotomy In Vivo Using Fibrin Adhesive The purpose of this Example was to compare the performance of the Fibrin adhesive in sealing around a suture line of an enterotomy incision in the small intestine of a living rabbit with that of the dextran-PEG adhesive, as described in Example 46.

The procedure used was the same as described in Example 46, except that Fibrin adhesive (250 µL) was applied to the enterotomy suture sites. The patch was allowed to cure for 2 min. In three out of five cases the adhesive had to be reapplied because the adhesive washed off the site due to bleeding. The peritoneum and abdomen were closed in layers using standard surgical procedure. The intestine surface was covered about 100% of the way around, leaving the mesentery uncovered.

At necropsy 3 days later, the adhesive application site was examined for gross tissue responses and the presence of the adhesive. The severity of erythema and edema were assessed using a scoring system that is consistent with the ISO intracutaneous reactivity test (ISO 10993-12). The examination revealed gross adhesions at the site due to presumed leakage. Furthermore, the adhesive had lifted off the intestinal surface and was attached mechanically to the suture ends. Histopathological analysis revealed inflammatory response due to the leak. This result demonstrates the superior in vivo adhesion and sealing ability of the dextran-PEG adhesive, described in Example 46, compared to the Fibrin adhesive.

Example 48

Sealing a Rabbit Resection In Vivo

The safety and efficacy of the hydrogel was further demonstrated by sealing around the suture line of a resection in the small intestine of a living rabbit. After the application of the adhesive around the sutures and incision it was allowed to cure. The animals were closed and fed normally and then were sacrificed 3 days later. The intestinal and adjoining tissues under and around the hydrogel adhesive patch were examined for edema, erythema, toxicity, inflammation, degradation of the hydrogel, adhesion to the intestinal wall and lack of adhesion tissue growth.

Five white New Zealand rabbits (1 year old, approximately 4 kg in weight) were fasted overnight. Prior to surgery, the animals were treated with buprenorphine, then anaesthetized with a mixture of ketamine and xylazine. A standard laparotomy procedure was performed to isolate a section of the duodenum of the small intestine. A single "marker" stitch of blue-dyed polypropylene suture material (Prolene®, Ethicon) was placed in the duodenum in the outer layer of intestinal tissue about 10 cm distal from the stomach. This was done to aid in locating the hydrogel patch at necropsy. A full incision through the small intestine was made about 12 cm distal from the stomach. The two ends of the intestine were rejoined using 9 stitches with 5-0 Vicryl sutures. A patch of hydrogel was applied to the small intestine over the stitches in the following manner. Using the delivery device described in Examples 1-16, with a motionless mixer having 8 mixing steps, 100 µL of oxidized dextran solution (30 wt %, 46% oxidation conversion, eq wt=160) mixed with 100 µL of 8-arm PEG amine solution (50 wt %; eq wt=1250) was delivered to the resection sites. The adhesive clotted the noticeable bleeding in place and was able to crosslink and become tack free within 15 sec. The patch was allowed to cure for 2 min and then the peritoneum and abdomen were closed in layers using standard surgical procedure. The intestine surface was covered about 100% of the way around, leaving the mesentery uncovered.

At necropsy 3 days later, the adhesive application site was examined for gross tissue responses and the presence of the adhesive. The severity of erythema and edema were assessed using a scoring system that is consistent with the ISO intracutaneous reactivity test (ISO 10993-12). The examination revealed good adhesion of the hydrogel adhesive in all cases and no observable inflammation. There were no fibrous adhesions or attachment to adjacent tissue. There was swelling of the hydrogel, but no deterioration of the polymer coating. Sections of about 12.5 cm of the intestine were excised from the rabbits and evaluated for leak pressure, as described in Examples 1-16. In all cases, the leak pressure was between 25 to 65 mm of mercury. Histopathological analysis revealed the biocompatibility of the hydrogel.

For comparison, rabbits were closed without the application of an adhesive. Necropsy 3 days later revealed gross adhesions at the site due to presumed leakage. Sections of about 12.5 cm of the intestine were excised from the rabbits and evaluated for leak pressure. In four of the cases, leakage occurred at essentially zero gauge pressure. The fifth sample achieved a pressure of about 90 mm of mercury. However, there were considerable adhesions at the anastomosis site. Histopathological analysis revealed inflammatory response due to leakage at the site.

Example 49

Comparative Example of Sealing a Rabbit Resection In Vivo Using Fibrin Adhesive

The purpose of this Example was to compare the performance of the Fibrin adhesive in sealing around a suture line of a resection in the small intestine of a living rabbit with that of the dextran-PEG adhesive, as described in Example 48.

The procedure used was the same as described in Example 48, except that the Fibrin adhesive (300 µL) was applied to the resection sites. The patch was allowed to cure for 2 min. In two out of the five cases, the adhesive had to be reapplied because the adhesive washed off the site due to bleeding. The patch was allowed to cure for 2 min and then the peritoneum and abdomen were closed in layers using standard surgical procedure. The intestine surface was covered about 100% of the way around, leaving the mesentery uncovered.

At necropsy 3 days later, the adhesive application site was examined for gross tissue responses and the presence of the adhesive. The severity of erythema and edema were assessed using a scoring system that is consistent with the ISO intracutaneous reactivity test (ISO 10993-12). The examination revealed gross adhesions at the site due to presumed leakage of fecal matter. Furthermore, the adhesive had lifted off the intestinal surface and was attached mechanically to the suture ends. Sections of about 12.5 cm of the intestine were excised from the rabbits and evaluated for leak pressure. In all but one case, leakage occurred at essentially zero gauge pressure. The one case had a leak pressure of about 25 mm of mercury. Histopathological analysis revealed inflammatory response due to the leakage. This result demonstrates the superior in vivo adhesion and sealing ability of the dextran-PEG adhesive, described in Example 48, compared to the Fibrin adhesive.

What is claimed is:
1. A kit comprising:
a) a first aqueous solution comprising an oxidized polysaccharide containing aldehyde groups, having a molecular weight of about 1,000 to about 1,000,000 Daltons, said oxidized polysaccharide having an equivalent weight per aldehyde group of about 90 to about 1500 Daltons, said solution containing from about 5% to about 40% by weight of the oxidized polysaccharide; and
b) a second aqueous solution comprising a water-dispersible, multi-arm polyether amine wherein at least three of the arms are terminated by a primary amine group, wherein the multi-arm polyether amine has a molecular weight of about 450 to about 200,000 Daltons, said solution containing from about 5% to about 70% by weight of the multi-arm polyether amine.

2. The kit according to claim 1 wherein the molecular weight of the oxidized polysaccharide is from about 3,000 to about 250,000 Daltons.

3. The kit according to claim 1 wherein the molecular weight of the multi-arm polyether amine is from about 2,000 to about 40,000 Daltons.

4. The kit according to claim 1 wherein the oxidized polysaccharide is selected from the group consisting of dextran, chitin, starch, agar, cellulose, and hyaluronic acid.

5. The kit according to claim 1 wherein the aldehyde groups on the oxidized polysaccharide of the first aqueous solution are in a stoichiometric excess relative to the amine groups on the multi-arm polyether amine of the second aqueous solution.

6. The kit according to claim 1 wherein the first and second aqueous solutions are sterilized.

7. The kit according to claim 1 wherein the first or second aqueous solution further comprises an additive selected from the group consisting of pH modifiers, viscosity modifiers, antimicrobials, colorants, healing promoters, surfactants, anti-inflammatory agents, thrombogenic agents, and radio-opaque compounds.

8. The kit according to claim 7 wherein said colorants are selected from the group consisting of FD&C Violet No. 2, D&C Green No. 6, D&C Green No. 5, and D&C Violet No. 2.

9. The kit according to claim 7 wherein said antimicrobial is triclosan.

10. The kit according to claim 1 wherein the first or second aqueous solution further comprises a pharmaceutical drug or therapeutic agent.

11. The kit according to claim 1 wherein the concentration of the oxidized polysaccharide in the first aqueous solution is from about 15% to about 30% by weight.

12. The kit according to claim 1 wherein the water-dispersible multi-arm polyether amine is selected from the group consisting of amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, amino-terminated dendritic polyamidoamines, and polyoxyalkylene triamines.

13. The kit according to claim 1 wherein the multi-arm polyether amine is a star polyethylene glycol comprising eight arms terminated by a primary amine group and having a molecular weight of 10,000 Daltons.

14. The kit according to claim 1 wherein the concentration of the multi-arm polyether amine in the second aqueous solution is from about 20% to about 50% by weight.

15. The kit according to claim 1 wherein the second aqueous solution further comprises at least one other multi-functional amine having one or more primary amine groups, said multi-functional amine being present at a concentration of about 5% to about 1000% by weight relative to the amount of the multi-arm polyether amine in the solution.

16. The kit according to claim 15 wherein the multi-functional amine is selected from the group consisting of water-dispersible multi-arm polyether amines, linear and branched diamines, branched polyamines, cyclic diamines, aminoalkyltrialkoxysilanes, aminoalkyldialkoxyalkylsilanes, dihydrazides, linear polymeric diamines, comb polyamines, dihydrazides and polyhydrazides.

17. The kit according to claim 1 further comprising a third solution comprising at least one other multi-functional amine having one or more primary amine groups, said solution containing about 5% to about 100% by weight of the multi-functional amine relative to the total weight of the solution.

18. The kit according to claim 17 wherein the multi-functional amine is selected from the group consisting of water-dispersible multi-arm polyether amines, linear diamines, branched diamines, branched polyamines, cyclic diamines, aminoalkyltrialkoxysilanes, dihydrazides, linear polymeric diamines, comb polyamines, dihydrazides and polyhydrazides.

19. The kit according to claim 17 wherein the third solution is sterilized.

20. A method for applying a coating to an anatomical site on tissue of a living organism comprising: applying to the site a) a first aqueous solution comprising an oxidized polysaccharide containing aldehyde groups, having a molecular weight of about 1,000 to about 1,000,000 Daltons, said oxidized polysaccharide having an equivalent weight per aldehyde group of about 90 to about 1500 Daltons, said solution containing from about 5% to about 40% by weight of the oxidized polysaccharide, followed by b) a second aqueous solution comprising a water-dispersible, multi-arm polyether amine wherein at least three of the arms are terminated by a primary amine group, wherein the multi-arm polyether amine has a molecular weight of about 450 to about 200,000 Daltons, said solution containing from about 5% to about 70% by weight of the multi-arm polyether amine, or the aqueous solution of (b) followed by the aqueous solution of (a), or premixing the aqueous solutions of (a) and (b) and applying the resulting mixture to the site before the resulting mixture completely cures.

21. A method for bonding at least two anatomical sites together comprising: applying to at least one site a) a first aqueous solution comprising an oxidized polysaccharide containing aldehyde groups, having a molecular weight of about 1,000 to about 1,000,000 Daltons, said oxidized polysaccharide having an equivalent weight per aldehyde group of about 90 to about 1500 Daltons, said solution containing from about 5% to about 40% by weight of the oxidized polysaccharide; applying to a least one of either the same site or one other site b) a second aqueous solution comprising a water-dispersible, multi-arm polyether amine wherein at least three of the arms are terminated by a primary amine group, wherein the multi-arm polyether amine has a molecular weight of about 450 to about 200,000 Daltons, said solution containing from about 5% to about 70% by weight of the multi-arm polyether amine; or premixing the solutions of (a) and (b) and applying the resulting mixture to at least one site before the resulting mixture completely cures; and contacting the at least two anatomical sites together.

22. The method of claim 20 or 21 wherein the molecular weight of the oxidized polysaccharide is from about 3,000 to about 250,000 Daltons.

23. The method of claim 20 or 21 wherein the molecular weight of the multi-arm polyether amine is from about 2,000 to about 40,000 Daltons.

24. The method of claim 20 or 21 wherein the oxidized polysaccharide is selected from the group consisting of dextran, chitin, starch, agar, cellulose, and hyaluronic acid.

25. The method of claim 20 or 21 wherein the aldehyde groups on the oxidized polysaccharide of the first aqueous solution are in a stoichiometric excess relative to the amine groups on the multi-arm polyether amine of the second aqueous solution.

26. The method of claim 20 or 21 wherein the first and second aqueous solutions are sterilized.

27. The method of claim 20 or 21 wherein the first or second aqueous solution further comprises an additive selected from the group consisting of pH modifiers, viscosity modifiers, antimicrobials, colorants, healing promoters, surfactants, anti-inflammatory agents, thrombogenic agents, and radio-opaque compounds.

28. The method of claim 27 wherein said colorants are selected from the group consisting of FD&C Violet No. 2, D&C Green No. 6, D&C Green No. 5, and D&C Violet No. 2.

29. The method of claim 27 wherein said antimicrobial is triclosan.

30. The method of claim 20 or 21 wherein the first or second aqueous solution further comprises a pharmaceutical drug or therapeutic agent.

31. The method of claim 20 or 21 wherein the concentration of the oxidized polysaccharide in the first aqueous solution is from about 15% to about 30% by weight.

32. The method of claim 20 or 21 wherein the water-dispersible multi-arm polyether amine is selected from the group consisting of amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, amino-terminated dendritic polyamidoamines, and polyoxyalkylene triamines.

33. The method of claim 20 or 21 wherein the water-dispersible multi-arm polyether amine is a polyethylene glycol comprising eight arms terminated by a primary amine group and having a molecular weight of 10,000 Daltons.

34. The method of claim 20 or 21 wherein the concentration of the multi-arm polyether amine in the second aqueous solution is from about 20% to about 50% by weight.

35. The method of claim 20 or 21 wherein the second aqueous solution further comprises at least one other multi-functional amine having one or more primary amine groups, said multi-functional amine being present at a concentration of about 5% to about 1000% by weight relative to the amount of the multi-arm polyether amine in the solution.

36. The method of claim 35 wherein the multi-functional amine is selected from the group consisting of water-dispersible multi-arm polyether amines, linear diamines, branched diamines, branched polyamines, cyclic diamines, aminoalkyltrialkoxysilanes, dihydrazides, linear polymeric diamines, comb polyamines, dihydrazides and polyhydrazides.

37. The method of claim 20 further comprising applying to the site c) a third solution comprising a multi-functional amine having one or more primary amine groups, wherein the solutions (a), (b), and (c) are applied in any order or premixing the solutions of (a), (b), and (c) and applying the resulting mixture to the site before the resulting mixture completely cures.

38. The method of claim 37 wherein the multi-functional amine is selected from the group consisting of water-dispersible multi-arm polyether amines, linear diamines, branched diamines, branched polyamines, cyclic diamines, aminoalkyltrialkoxysilanes, dihydrazides, linear polymeric diamines, comb polyamines, dihydrazides and polyhydrazides.

39. The method of claim 21 further comprising applying to at least one site c) a third solution comprising a multi-functional amine having one or more primary amine groups, or premixing the solutions of (a), (b), and (c) and applying the resulting mixture to the site before the resulting mixture completely cures, and contacting the at least two anatomical sites together.

40. The method of claim 39 wherein the multi-functional amine is selected from the group consisting of water-dispersible multi-arm polyether amines, linear diamines, branched diamines, branched polyamines, cyclic diamines, aminoalkyltrialkoxysilanes, dihydrazides, linear polymeric diamines, comb polyamines, dihydrazides and polyhydrazides.

41. The method of claim 37 or 39 wherein the third solution is sterilized.

42. The method of claim 20 wherein the anatomical site is a wound on the skin and the method is used for treatment of topical wounds.

43. The method of claim 20 wherein the anatomical site is on an intestine or blood vessel and the method is used in an anastomosis procedure.

44. The method of claim 20 wherein the anatomical site is on the eye and the method is used to seal a corneal incision.

45. The method of claim 20 wherein the method is used to prevent adhesions between adjacent anatomical sites.

46. The method of claim 20 wherein the first or second aqueous solution further comprises a pharmaceutical drug or therapeutic agent and the method is used for drug delivery to the anatomical site.

47. The method of claim 20 wherein the anatomical site is the bladder and the method is used to treat urinary incontinence.

* * * * *